(12) United States Patent
Murakami et al.

(10) Patent No.: US 8,955,670 B2
(45) Date of Patent: Feb. 17, 2015

(54) ABSORBENT ARTICLE ROTATING APPARATUS AND METHOD OF ROTATING AN ABSORBENT ARTICLE

(75) Inventors: Seiji Murakami, Kagawa (JP); Youji Shinomori, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 13/823,223

(22) PCT Filed: Sep. 26, 2011

(86) PCT No.: PCT/JP2011/071799
§ 371 (c)(1),
(2), (4) Date: Jun. 17, 2013

(87) PCT Pub. No.: WO2012/043434
PCT Pub. Date: Apr. 5, 2012

(65) Prior Publication Data
US 2013/0270068 A1    Oct. 17, 2013

(30) Foreign Application Priority Data

Sep. 30, 2010  (JP) .................................. 2010-222492

(51) Int. Cl.
| | | |
|---|---|---|
| A61F 13/472 | (2006.01) | |
| B65G 47/244 | (2006.01) | |
| A61F 13/15 | (2006.01) | |
| A61F 13/551 | (2006.01) | |

(52) U.S. Cl.
CPC ........ *B65G 47/244* (2013.01); *A61F 13/15747* (2013.01); *A61F 13/15764* (2013.01); *A61F 13/5514* (2013.01)

USPC ............ 198/817; 198/412; 198/416; 198/617

(58) Field of Classification Search
USPC .................. 198/412, 416, 817, 617
See application file for complete search history.

(56) References Cited

U.S. PATENT DOCUMENTS

| | | | | |
|---|---|---|---|---|
| 4,807,739 A | * | 2/1989 | Wolf et al. ..................... | 198/415 |
| 5,518,103 A | * | 5/1996 | Achelpohl et al. ............ | 198/416 |
| 5,660,262 A | * | 8/1997 | Landrum et al. .............. | 198/411 |
| 5,725,703 A | * | 3/1998 | Gerloff ......................... | 156/130 |

(Continued)

FOREIGN PATENT DOCUMENTS

| | | |
|---|---|---|
| CN | 1692065 A | 11/2005 |
| DE | 9210809 U1 | 10/1992 |

(Continued)

OTHER PUBLICATIONS

PCT/JP2011/071799 International Search Report, dated Dec. 13, 2011.

(Continued)

*Primary Examiner* — Douglas Hess
(74) *Attorney, Agent, or Firm* — Lowe Hauptman & Ham LLP

(57) ABSTRACT

An absorbent article rotating apparatus includes a transporting section that transports an absorbent article along a transport direction with the absorbent article being sandwiched between a pair of belts, and a fixed member that rotates the absorbent article by coming into contact with a portion of an edge of the absorbent article, the portion being exposed from the belts, the edge being at a downstream side in the transport direction, the fixed member being fixed at a predetermined position in the transport direction.

7 Claims, 8 Drawing Sheets

(56) References Cited

U.S. PATENT DOCUMENTS

| | | | |
|---|---|---|---|
| 6,095,316 A * | 8/2000 | Redden | 198/415 |
| 6,126,383 A * | 10/2000 | Franklin et al. | 414/792 |
| 7,694,709 B2 * | 4/2010 | Kaagman et al. | 156/360 |
| 7,798,308 B2 * | 9/2010 | Ranger | 198/415 |

FOREIGN PATENT DOCUMENTS

| | | | |
|---|---|---|---|
| DE | 102007041254 A1 | 3/2009 | |
| GB | 2285961 A | 8/1995 | |
| JP | 63107793 U | 7/1988 | |
| JP | 63317576 A | 12/1988 | |
| JP | 2002240985 A | 8/2002 | |
| JP | 2005222128 A | 8/2005 | |
| WO | 2010101280 A1 | 9/2010 | |

OTHER PUBLICATIONS

Extended European Search Report issued Aug. 14, 2014, corresponds to European patent application No. 11828988.3.
Office Action issued Jun. 4, 2014, corresponds to Chinese patent application No. 201180047111.2.

* cited by examiner

ABSORBENT ARTICLE ROTATING APPARATUS AND METHOD OF ROTATING AN ABSORBENT ARTICLE

RELATED APPLICATIONS

The present application is a National Phase of PCT/JP2011/071799, filed Sep. 26, 2011, and is based on, and claims priority from, Japanese Application No. 2010-222492 filed Sep. 30, 2010.

TECHNICAL FIELD

The present invention relates to an apparatus that rotates an absorbent article such as a sanitary napkin and a method of rotating an absorbent article.

BACKGROUND ART

Sanitary napkins and disposable diapers are exemplary absorbent articles that absorb liquid excretion such as urine and menstrual blood. On a production line of those absorbent articles, there is a case where an absorbent article is rotated to change an orientation of the absorbent article. In order to rotate an absorbent article, a method has been proposed in which the absorbent article is held by suction onto a suction holding plate provided on a rotation drum surface and the suction holding plate is rotated by a cam mechanism (e.g., see PTL 1).

CITATION LIST

Patent Literature

[PTL 1] JP-A-63-317576

SUMMARY OF INVENTION

Technical Problem

However, the above mentioned method requires an apparatus with a complex mechanism such as a cam mechanism.

The present invention has been contrived in view of the drawbacks described above, and its object is to provide an apparatus that rotates an absorbent article in a facilitated manner and a method of rotating an absorbent article in a facilitated manner.

Solution to Problem

In order to achieve the above-described advantages, a principal aspect of the invention is an absorbent article rotating apparatus including:

a transporting section that transports an absorbent article along a transport direction with the absorbent article being sandwiched between a pair of belts; and a fixed member that rotates the absorbent article by coming into contact with a portion of an edge of the absorbent article, the portion being exposed from the belts, the edge being at a downstream side in the transport direction, the fixed member being fixed at a predetermined position in the transport direction.

Also provided is a method of rotating an absorbent article, the method including:

transporting an absorbent article along a transport direction with the absorbent article being sandwiched between a pair of belts; and rotating the absorbent article by causing a portion of an edge of the absorbent article to come into contact with a fixed member, the portion being exposed from the belts, the edge being at a downstream side in the transport direction, the fixed member being fixed at a predetermined position in the transport direction.

Features of the invention other than the above will become clear by the description of the present specification and the accompanying drawings.

Advantageous Effects of Invention

According to the present invention, an apparatus that rotates an absorbent article in a facilitated manner and a method of rotating an absorbent article in a facilitated manner can be obtained.

MODE FOR CARRYING OUT THE INVENTION

Figure 1A:
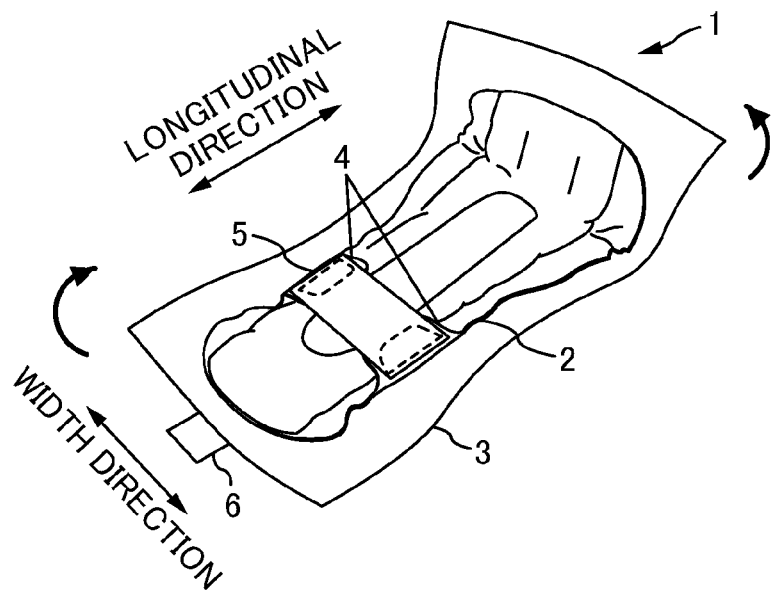
FIG. 1A is an explanatory diagram illustrating how a main body section of a sanitary napkin is individually wrapped with a wrapping material and FIG. 1B is a plan view of the individually wrapped sanitary napkin.

At least the following matters will become apparent from descriptions of this present specification and of the accompanying drawings.

According to an aspect of the present invention, an absorbent article rotating apparatus includes: a transporting section that transports an absorbent article along a transport direction with the absorbent article being sandwiched between a pair of belts; and a fixed member that rotates the absorbent article by coming into contact with a portion of an edge of the absorbent article, the portion being exposed from the belts, the edge being at a downstream side in the transport direction, the fixed member being fixed at a predetermined position in the transport direction.

With such absorbent article rotating apparatus, the absorbent article can be rotated with a simple apparatus configuration. Therefore, the apparatus can be prevented from becoming bulky and costs can be reduced.

Provided is an absorbent article rotating apparatus as described above, further including: a rotation restricting section that restricts rotation of the absorbent article, the rotation restricting section being provided at a position where the rotation restricting section can come into contact with the edge of the absorbent article rotated by the fixed member.

With such absorbent article rotating apparatus, excessive rotation of the absorbent article can be suppressed.

Provided is an absorbent article rotating apparatus in which the fixed member has a wall surface lying along a direction that intersects with the transport direction, the rotation restricting section being a wall surface that forms an angle with the wall surface of the fixed member, the angle being based on a desired amount of rotation of the absorbent article.

With such absorbent article rotating apparatus, the absorbent article can be rotated with a desired amount of rotation.

Provided is an absorbent article rotating apparatus as described above, further including a pressing member, in which the pair of belts sandwich the absorbent article in a thickness direction of the absorbent article, and the pressing member presses the absorbent article in the thickness direction via the belts when the edge of the absorbent article and the fixed member come into contact.

With such absorbent article rotating apparatus, slippage between the belts and the absorbent article can be prevented and a rotational force can be exerted on the absorbent article.

Provided is an absorbent article rotating apparatus as described above, further including a first wall section, in which the fixed member comes into contact with the edge of the absorbent article at a portion of the edge exposed from the belts at one side in an intersecting direction that intersects with the transport direction, the first wall section being provided at a position downstream of the fixed member in the transport direction and at a position more to the other side in the intersecting direction than the belts, the first wall section being inclined to the one side in the intersecting direction from an upstream side in the transport direction to the downstream side.

With such absorbent article rotating apparatus, a relative position between the belts and the absorbent article that have been offset by the rotation of the absorbent article can be returned. Also, with the absorbent article coming into contact with the first wall section, a lack in rotation of the absorbent article can be compensated.

Provided is an absorbent article rotating apparatus described above, further including: a second wall section provided at a position downstream of the first wall section in the transport direction; and an opposed wall section that opposes at least a part of the first wall section as well as the second wall section across the belts in the intersecting direction, a gap between the first wall section and the opposed wall section in the intersecting direction being narrower at a position on the downstream side in the transport direction than at a position on the upstream side.

With such absorbent article rotating apparatus, the absorbent article can be transported smoothly while adjusting the orientation of the absorbent article.

Provided is an absorbent article rotating apparatus as described above, in which a gap in the intersecting direction between the opposed wall section opposing the second wall section and a central section of the belts in the intersecting direction is greater than a gap in the intersecting direction between an end section on the other side in the intersecting direction of the fixed member and the central section of the belts.

With such absorbent article rotating apparatus, the absorbent article can come into contact with the fixed member, and the central section of the absorbent article after rotation can be made to approach to the central portion of the belts.

Provided is an absorbent article rotating apparatus as described above, in which the absorbent article is an article in which a main body section of the absorbent article is individually wrapped with a wrapping material, a distance in the intersecting direction between the second wall section and the opposed wall section being smaller than a length of the edge on the downstream side in the transport direction of the absorbent article after rotation and greater than or equal to a length of the edge on the downstream side in the transport direction of the main body section after rotation.

With such absorbent article rotating apparatus, the orientation of the absorbent article can be adjusted without compressing the main body section of the absorbent article.

A further aspect of the invention is a method of rotating an absorbent article, the method including: transporting an absorbent article along a transport direction with the absorbent article being sandwiched between a pair of belts; and rotating the absorbent article by causing a portion of an edge of the absorbent article to come into contact with a fixed member, the portion being exposed from the belts, the edge being at a downstream side in the transport direction, the fixed member being fixed at a predetermined position in the transport direction.

With such absorbent article rotating apparatus, the absorbent article can be rotated in a facilitated manner.

===Sanitary Napkin (Absorbent Article)===

In the description below, an individually wrapped sanitary napkin will be described as an example of an "absorbent article."

Figure 1B:
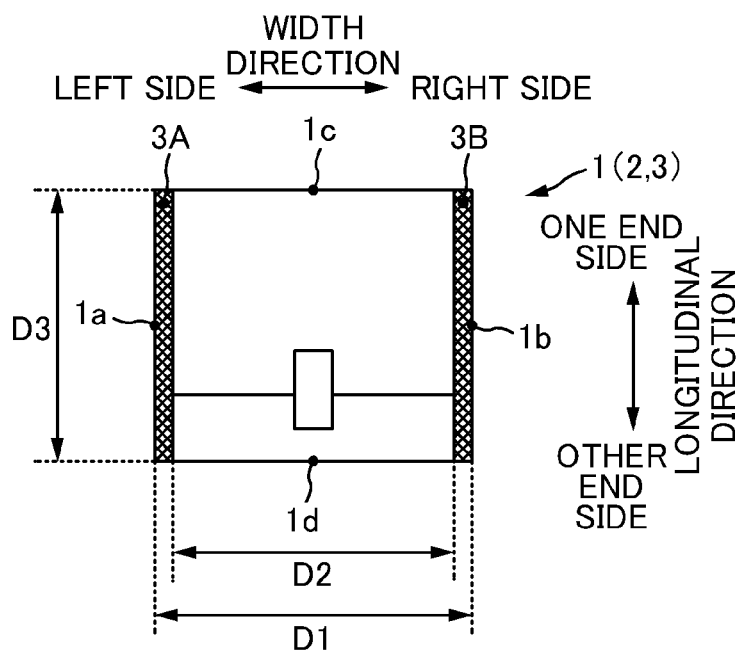

FIG. 1A is an explanatory diagram illustrating how a main body section of a sanitary napkin (hereinafter referred to as a napkin main body section 2) is individually wrapped with a wrapping material 3, and FIG. 1B is a plan view of the individually wrapped sanitary napkin (hereinafter referred to as a napkin 1). The napkin main body section 2 is of a substantially rectangular shape that is elongated in a longitudinal direction, and has a liquid permeable front face sheet (e.g., a nonwoven fabric), a liquid impermeable back face sheet (e.g., a sheet of polyethylene or polypropylene) and an absorbent base material that absorbs a liquid (e.g., a pulp fiber or a high-absorbent polymer), with the absorbent base material being provided between the front face sheet and the back face sheet.

When individually wrapping the napkin main body section 2, first, as shown in FIG. 1A, wing sections 4 of the napkin main body section 2 are bent towards a front face side of the napkin main body section 2 and a protection sheet 5 is provided thereon. Thereafter, the napkin main body section 2 is folded twice in the longitudinal direction together with the rectangular wrapping material 3 (e.g., nonwoven fabric or a sheet of polyethylene) that is provided on a back face side of the napkin main body section 2, in such a manner that a front face of the napkin main body section 2 is situated inside. Then, an overlapping portion of the folded napkin main body section 2 and the wrapping material 3 is fastened with a tape 6.

As shown in FIG. 1B, edge sections of the folded wrapping material 3 at the right and left thereof in a width direction (a direction intersecting with the longitudinal direction) are adhered. The adhered edge sections (cross-hatched sections in the drawings) are referred to as adhered sections 3A and 3B. A method of adhering the adhered sections 3A and 3B may be, for example, a method in which an adhesive agent is applied or a pressure bonding method by performing an embossing process. In this manner, the napkin main body section 2 is contained in the wrapping material 3.

For the sake of explanation below, as shown in FIG. 1B, with the napkin 1 being spread in the width direction, a size of the wrapping material 3 (napkin 1) in the width direction is defined as "D1", a size of the wrapping material 3 (napkin 1) in the width direction excluding the adhered sections 3A, 3B is defined as "D2", and a size of the wrapping material 3 (napkin 1) in the longitudinal direction is defined as "D3".

The napkin main body section 2 contained in the wrapping material 3 is located at a portion of the wrapping material 3 other than the adhered sections 3A and 3B. Therefore, a maximum size of the napkin main body section 2 in the width direction is less than or equal to the size "D2" of the wrapping material 3 in the width direction excluding the adhered sections 3A and 3B. Usually, the wrapping material 3 is provided with a space without the napkin main body section 2 at a portion other than the adhered sections 3A and 3B, to give some clearance. However, to facilitate the explanation here, the napkin main body section 2 is situated from the adhered section 3A on the left side in the width direction to the adhered section 3B on the right side in the width direction of the wrapping material 3. In other words, the maximum size of the napkin main body section 2 in the width direction is equal to the size of the wrapping material 3 in the width direction excluding the adhered sections 3A and 3B, i.e., "D2".

Also, for the explanation below, concerning the napkin 1, an edge lying along the longitudinal direction and located on the left side in the width direction is referred to as a "first edge 1a", an edge similarly lying along the longitudinal direction and located on the right side in the width direction is referred to as a "second edge 1b", an edge lying along the width direction and located on one end side in the longitudinal direction is referred to as a "third edge 1c", and an edge similarly lying along the width direction and located on the other end side in the longitudinal direction is referred to as a "fourth edge 1d". Further, a direction in which there is an overlap in the napkin 1 (in FIG. 1B, a direction penetrating through a plane of paper) is referred to as a "thickness direction", and a face of the napkin 1 fastened by the tape 6 is referred to as a "front face" and a face opposite thereto is referred to as a "back face".

===Rotating Apparatus and Rotating Method for a Sanitary Napkin (Absorbent Article)===

Figure 2:
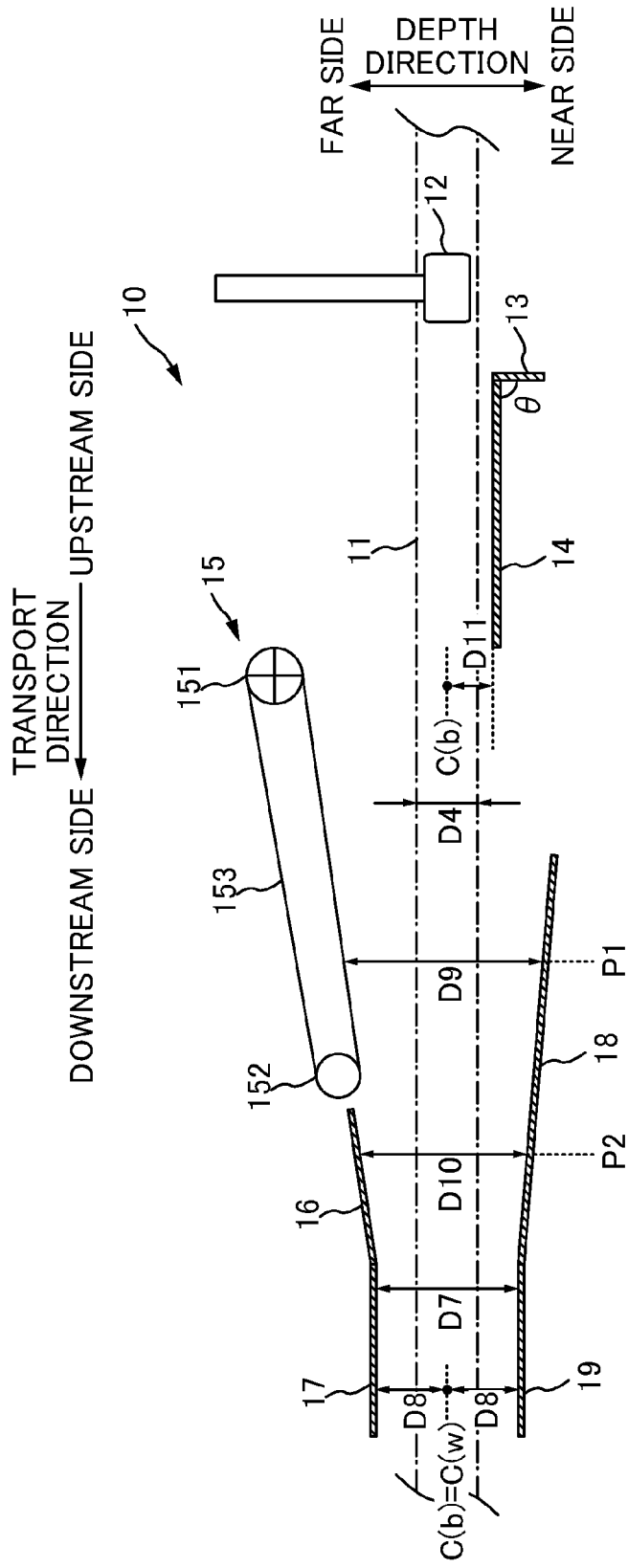
FIG. 2 is an explanatory diagram of a napkin rotating apparatus.
Figure 3:
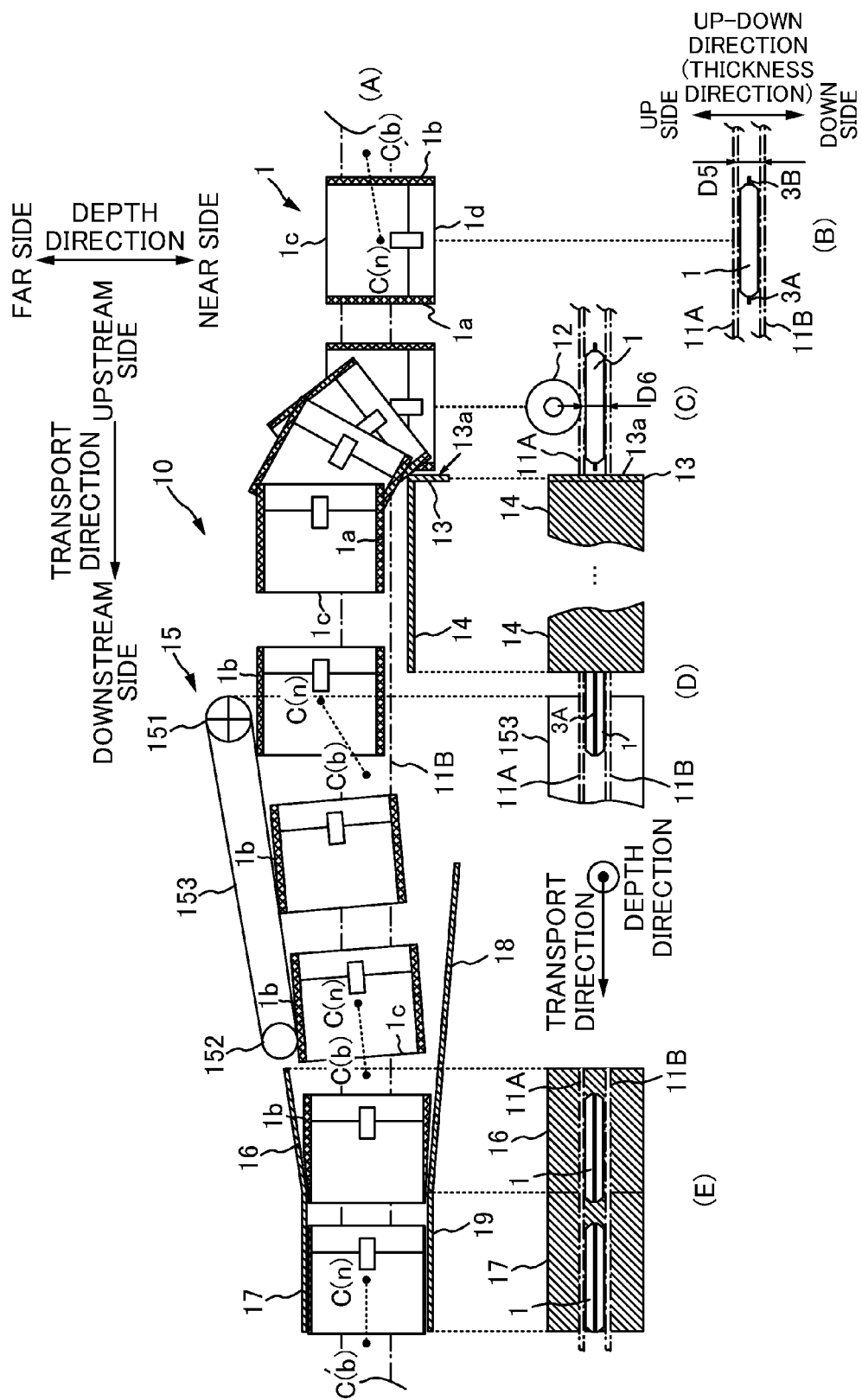
FIG. 3 is an explanatory diagram illustrating how a napkin is rotated by the rotating apparatus.

FIG. 2 is an explanatory diagram of a rotating apparatus 10 for the napkin 1, and FIG. 3 is a diagram illustrating how the napkin 1 is rotated by the rotating apparatus 10. In general, the individually wrapped napkin 1 is distributed in a state where it is packed in a bag with a plurality of napkins 1. Also, there may be a case where an orientation of the napkin 1 in a manufacturing process is different from an orientation of the napkin 1 in a packing process. In such a case, the napkin 1 needs to be rotated to change the orientation of the napkin 1. However, for example, if the napkin 1 is to be rotated by placing the napkin 1 on a plate provided at a surface of a rotating drum and turning the plate with a cam mechanism installed in the rotating drum, an apparatus having a complex mechanism will be required. Also, the apparatus will become bulky.

Therefore, the present embodiment has for its object to provide an apparatus that easily rotates the napkin 1 and a method that easily rotates the napkin 1.

Here, as shown in FIG. 3, at part (A), it is assumed that the napkin 1, the first edge 1a of which being located on a downstream side in the transport direction, needs to be oriented in such a manner that the third edge 1c comes to the downstream side in the transport direction for packing into a bag (i.e., for a subsequent process). That is to say, taking the thickness direction of the napkin 1 as a rotation axis direction, the napkin 1 needs to be rotated through 90 degrees in the transport direction of the napkin 1 (in FIG. 3, at part (A), in a counterclockwise direction).

First, the rotating apparatus 10 for the napkin 1 of the present embodiment will be described.

As shown in FIG. 2, the rotation apparatus 10 has a transporting section that transports the napkin 1 from the upstream side to the downstream side in the transport direction, a pressing roller 12, a fixed wall 13, a rotation restricting wall 14, an inclined conveyor 15, a far side inclined wall 16, a far side final adjustment wall 17, a near side inclined wall 18 and a near side final adjustment wall 19. Note that FIG. 2 and part (A) in FIG. 3 are top views of the rotating apparatus 10, and parts (B) to (E) in FIG. 3 are cross-sectional views of a part of the rotating apparatus 10 and the napkin 1. In FIG. 3, at part (A), a part of the transport belt 11 and the pressing roller 12 have been omitted, and in FIG. 3, at part (E), the near side inclined wall 18 and the near side final adjustment wall 19 have been omitted in the drawing. Concerning the rotating apparatus 10, a direction that intersects with the transport direction of the napkin 1 is referred to as a "depth direction (corresponds to the intersecting direction), and one side in the depth direction is referred to as "a near side" and the other side in the depth direction is referred to as "a far side".

The transporting section has a pair of transport belts 11 that oppose in an up-down direction (in FIG. 2, a direction penetrating the plane of paper) of the rotating apparatus 10 and a driving source (e.g., a roller and a motor, not shown) that drives the transport belts 11. As shown in FIG. 3, at part (B), the transport belt 11 sandwiches the napkin 1 in the thickness direction of the napkin 1. In other words, the napkin 1 is transported in the transport direction in a state where it is sandwiched between the pair of transport belts 11 opposing in the up-down direction of the rotating apparatus 10. It is to be noted that, regarding the pair of transport belts 11, a portion of the transport belt 11 that is in contact with a front face of the napkin 1 is referred to as "an upper transport belt 11A" and a portion of the transport belt 11 that is in contact with a back face of the napkin 1 is referred to as "a lower transport belt 11B".

The pressing roller 12 is provided upstream of the fixed wall 13 in the transport direction and, as shown in FIG. 3, at part (C), provided so as to come into contact with an upper face of an upper transport belt 11A. Then, the pressing roller 12 presses the napkin 1 in the thickness direction from an upper side in the up-down direction of the rotating apparatus 10 via the upper transport belt 11A. It is to be noted that the pressing roller 12 may be a driving roller that voluntarily rotates by a motor and the like, or may be a driven roller that rotates with a movement of the transport belt 11 in the transport direction.

The fixed wall 13 is a wall that extends along the depth direction and provided at a predetermined position in the transport direction (a position downstream of the pressing roller 12 in the transport direction) and is provided in a fixed manner at a position on a nearer side with respect to the transport belts 11 in the depth direction.

The rotation restricting wall 14 is a wall that forms a predetermined angle θ with the fixed wall 13 and is provided at a position downstream of the fixed wall 13 in the transport direction and on the nearer side with respect to the transport belts 11 in the depth direction. Here, the angle θ formed by the fixed wall 13 and the rotation restricting wall 14 is "90 degrees." Therefore, the rotation restricting wall 14 is a wall surface that extends along the transport direction.

The inclined conveyor 15 (belt conveyor) is provided at a position downstream of the rotation restricting wall 14 in the transport direction and on a farther side with respect to the transport belts 11 in the depth direction, and has a driving roller 151 situated on the upstream side in the transport direction, a driven roller 152 situated on the downstream side in the transport direction and a broad belt 153. The belt 153 that is closed in a looped manner is provided across the driving roller 151 and the driven roller 152 and circulates around the two rollers 151 and 152 in accordance with the rotation of the driving roller 151. Also, the driven roller 152 situated on the downstream side in the transport direction is situated at the nearer side in the depth direction with respect to the driving roller 151 situated on the upstream side in the transport direction. Therefore, from the upstream side to the down stream side in the transport direction, the belt 153 is inclined to the nearer side (the transport belt 11 side) in the depth direction.

The far side inclined wall 16 is a wall surface that is provided at a position downstream of the inclined conveyor 15 in the transport direction and to the farther side in the depth direction with respect to the transport belt 11, and that extends along the transport direction. Also, similarly to the inclined conveyor 15, the far side inclined wall 16 is inclined to the near side in the depth direction (the conveyor belt 11 side) from the upstream side to the downstream side in the transport direction. It is to be noted that a position in the depth direction of an end portion at the downstream side in the transport direction of the belt 153 of the inclined conveyor 15 is substantially at the same position as a position in the depth direction of an end portion at the upstream side in the transport direction of the far side inclined wall 16. Therefore, surfaces on the near side in the depth direction of the belt 153 of the inclined conveyor 15 and the far side inclined wall 16 are inclined in a substantially linear and continuous manner from the upstream side to the downstream side of the transport direction.

The far side final adjustment wall 17 is a wall surface extending along the transport direction and provided at a position downstream of the far side inclined wall 16 in the transport direction and at a position on the farther side in the depth direction with respect to the transfer belt 11s. Here, the far side inclined wall 16 and the far side final adjustment wall 17 are not separated apart and arranged in a continuous manner in the transport direction.

The near side inclined wall 18 is provided in such a manner that it opposes, across the transport belts 11, a portion of the inclined conveyor 15 and the far side inclined wall 16 in the depth direction, which portion being on the downstream side in the transport direction. Also, the near side inclined wall 18 is inclined to the far side (the transfer belt 11 side) in the depth direction from the upstream side to the downstream side in the transport direction.

The near side final adjustment wall 19 is a wall surface that extends along the transport direction and is provided in such a manner that it opposes, across the transport belts 11, the far side final adjustment wall 16 in the depth direction. The near side inclined wall 18 and the near side final adjustment wall 19 are not spaced apart and are arranged in a continuous manner.

Further, as shown in parts (C) through (E) of FIG. 3, the fixed wall 13, the rotation restricting wall 14, the belt 153 of the inclined conveyor 15, the far side inclined wall 16, the far side final adjustment wall 17, as well as the near side inclined wall 18 and the near side final adjustment wall 19, which are not shown, are members each having a height in the up-down direction of the rotating apparatus 10 and the members are provided between a position higher than the upper transport belt 11A and a position lower than the lower transport belt 11B. Therefore, these members are provided, in the up-down direction of the rotating apparatus 10, at positions (levels) where they can come into contact with the napkin 1 that is transported in a state of being sandwiched between the transport belts 11.

Further, the fixed wall 13 and the rotation restricting wall 14 may be a one-piece member (e.g., a sheet metal bent at 90 degrees) or may be separate members. Similarly, the far side inclined wall 16 and the far side final adjustment wall 17 may be a one-piece member or may be separate members, and the near side inclined wall 18 and the near side final adjustment wall 19 may be a one-piece member or may be separate members. It is to be noted that the members arranged continuously in the transport direction are preferably provided as a one-piece member, since the napkin 1 transported in the transport direction is less likely to be caught and the napkin 1 can be transported smoothly.

Next, a method of rotating the napkin 1 with the rotating apparatus 10 will be described.

As shown in FIG. 3, the individually wrapped napkin 1 is transported in a state where it is sandwiched between the pair of transport belts 11. At this time, the first edge 1a and the second edge 1b that are provided along a longitudinal direction of the napkin 1 are lying along the depth direction of the rotating apparatus 10, and the third edge 1c and the fourth edge 1d that are provided along a width direction of the napkin 1 are lying along the transport direction of the rotating apparatus 10. The first edge 1a of the napkin 1 is on the downstream side in the transport direction and the first edge 1a corresponds to the "edge on the downstream side in the transport direction of the napkin 1".

Further, a width (size in the depth direction) "D4 (see FIG. 2)" of the transport belts 11 is shorter than a size in the longitudinal direction (size in the depth direction) "D3 (see FIG. 1B)" of the napkin 1. Therefore, as shown in FIG. 3, at part (A), the one end side in the longitudinal direction (e.g., the third edge 1c) of the napkin 1 is exposed from the transport belts 11 at the far side in the depth direction and the other end side in the longitudinal direction (e.g., the fourth edge 1d) of the napkin 1 is exposed from the transport belts 11 at the near side in the depth direction.

Thus, by transporting the napkin 1, as shown in FIG. 3, at parts (A) and (C), the first edge 1a (the edge on the downstream side in the transport direction) of the napkin 1 comes into contact with the fixed wall 13. In detail, a portion of the first edge 1a of the napkin 1 exposed from the transport belts 11 at the near side in the depth direction comes into contact with the wall surface (hereinafter referred to as a contact surface 13a) of the fixed wall 13 on the upstream side in the transport direction. Then, a rotational force in a counterclockwise direction is exerted on the napkin 1 and the napkin 1 rotates in the counterclockwise direction. As a result, the napkin 1, the first edge 1a of which being located on the downstream side in the transport direction, can be oriented in such a manner that the third edge 1c comes to the downstream side in the transport direction for packing into a bag (for a subsequent process).

Figure 4:
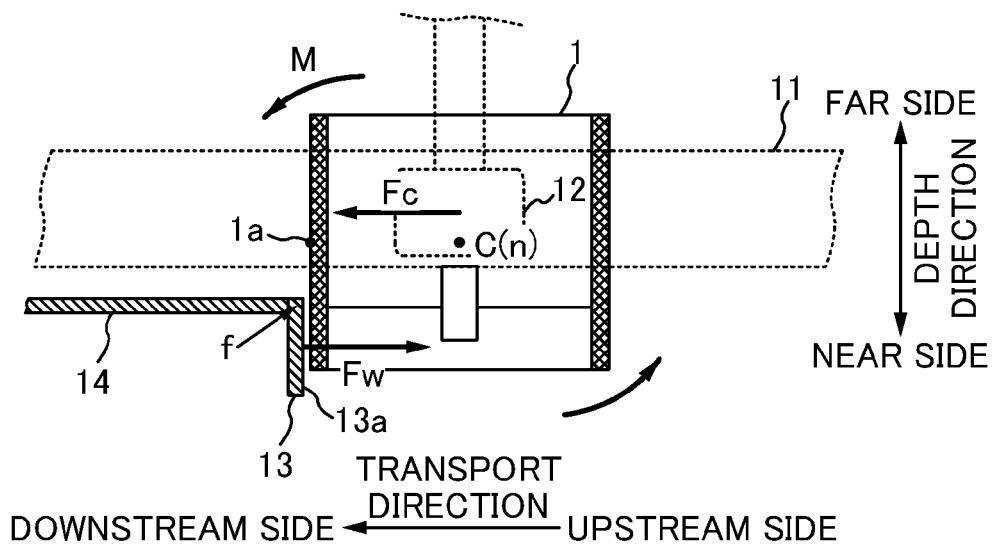
FIG. 4 is an explanatory diagram of forces exerted on a napkin.

FIG. 4 is a diagram illustrating forces exerted on a napkin 1. The napkin 1 in the rotating apparatus 10 experiences a force Fc that tends to move the napkin 1 from the upstream side to the downstream side in the transport direction by the transport belts 11 (transporting section). On the other hand, when the first edge 1a of the napkin 1 comes into contact with the fixed wall 13, the napkin 1 that tends to move to the downstream side in the transport direction experience a force (reaction force) Fw that tends to push the napkin 1, from the contact surface 13a of the fixed wall 13, back to the upstream side in the transport direction. In other words, when the first edge 1a of the napkin 1 comes into contact with the fixed wall 13, the napkin 1 experiences the force Fc acting along the transport direction and towards the downstream side in the transport direction and the force Fw acting along the transport direction and towards the upstream side in the transport direction. Then, these two forces Fc and Fw act as a couple and a rotational force (a moment M) is applied to the napkin 1. It is to be noted that the napkin 1 rotates in the counterclockwise direction with a pivot f being an end portion of the fixed wall 13 on the upstream side in the transport direction and that is an end portion on the far side in the depth direction.

In other words, with the rotating apparatus 10 of the present embodiment, the napkin 1 is rotated by transporting the napkin 1 along the transport direction in a state where the napkin 1 is sandwiched between the pair of transport belts 11 and causing the portion of an edge (first edge 1a) of the napkin 1 at a downstream side in the transport direction, which portion being exposed from the transport belts 11, to come into contact with the fixed wall 13.

Therefore, the napkin 1 can be rotated with the rotating apparatus 10 having a simple structure in which the fixed wall 13 is simply provided on the transport path of the napkin 1. Accordingly, with the rotating apparatus of the present embodiment, cost can be reduced since a complex mechanism is required and the space can be saved since the apparatus can be avoided from becoming bulky.

In the rotating apparatus 10 of the present embodiment, the portion of the napkin 1 that is exposed from the transfer belts 11 at the near side in the depth direction is caused to come into contact with the fixed wall 13. Therefore, the fixed wall 13 is provided on the nearer side in the depth direction with respect to the transport belts 11. Accordingly, the transport belts 11 and the fixed wall 13 can be prevented from being caught and the napkin 1 can be transported smoothly.

As has been described above (as shown in FIG. 3, at part (C)), the fixed wall 13 is a wall surface that has a height in the up-down direction of the rotating apparatus 10. Therefore, even if the position in the up-down direction of the napkin 1 upon coming into contact with the fixed wall 13 becomes slightly offset, the first edge 1a of the napkin 1 can be securely caused to come into contact with the fixed fall 13 and the napkin 1 can be rotated.

As shown in FIG. 3, at part (A), the napkin 1 before coming into contact with the fixed wall 13 is provided in such a manner that a central section C(n) of the napkin 1 in the depth direction is located on the nearer side (on the fixed wall 13 side) with respect to a central section C(b) of the transport belts 11 in the depth direction. In other words, the napkin 1 is more exposed on the nearer side (on the fixed wall 13 side) with respect to the transport belts 11. Therefore, even if the position of the napkin 1 becomes somewhat offset in the depth direction upon coming into contact with the fixed wall 13, the first edge 1a of the napkin 1 can be securely brought into contact with the fixed wall 13 and the napkin 1 can be rotated. However, it is not limited thereto, and the position of the center section C(n) of the napkin 1 in the depth direction may be aligned with the center section C(b) of the transport belts 11 in the depth direction in such a manner that the napkin 1 is securely sandwiched between the transport belts 11.

On the other hand, in a case where a portion of the napkin 1 (first edge 1a) that comes into contact with the fixed wall 13 is large, the reaction force Fw from the fixed wall 13 becomes strong and it will be difficult to rotate the napkin 1. Accordingly, as shown in FIG. 4, the center section C(n) of the napkin 1 in the depth direction is located at a farther side in the depth direction (the side opposite the fixed wall 13) with respect to the end section of the fixed wall 13 on the far side in the depth direction (i.e., pivot f). In such a manner, it is possible to prevent the portion of the napkin 1 that comes into contact with the fixed wall 13 from becoming too large that it becomes difficult to rotate the napkin 1.

With the rotating apparatus 10 of the present embodiment, as shown in FIG. 3, at part (C), when the first edge 1a (an edge on the downstream side in the transport direction) of the napkin 1 and the fixed wall 13 come into contact, the pressing roller 12 presses the napkin 1 in the thickness direction via the transport belts 11. In other words, a distance D6 between the transport belts 11A, 11B in the up-down direction when the napkin 1 and the fixed wall 13 are in contact (part (C) in FIG. 3) is made smaller than a distance D5 between the transport belts 11A, 11B in the up-down direction when the napkin 1 and the fixed wall 13 are not in contact (part (B) in FIG. 3). In this manner, a force exerted by the transport belts 11 when sandwiching the napkin 1 becomes stronger when the first edge 1a of the napkin 1 and the fixed wall 13 come into contact and the sliding between the transport belts 11 and the napkin 1 can be prevented. As a result, the transport belts 11 (transporting section) can securely exert the force Fc onto the napkin 1, which force Fc causing the napkin 1 to be moved downwards in the transport direction, and the napkin 1 can be rotated.

Here, as shown in FIG. 3, at part (C), the pressing roller 12 presses the central section along the width direction of the napkin 1. Therefore, it is preferable to provide the pressing roller 12 at a position which is offset to the upstream side in the transport direction from the fixed wall 13 by half a length of the widthwise size of the napkin 1 (D1/2). In order that the pressing roller 12 can press the napkin 1 from above, it is preferable the pressing roller 12 is provided in such a manner that the lower end surface of the pressing roller 12 is located at a position below the position of the upper transport belt 11A in the up-down direction.

Figure 5:
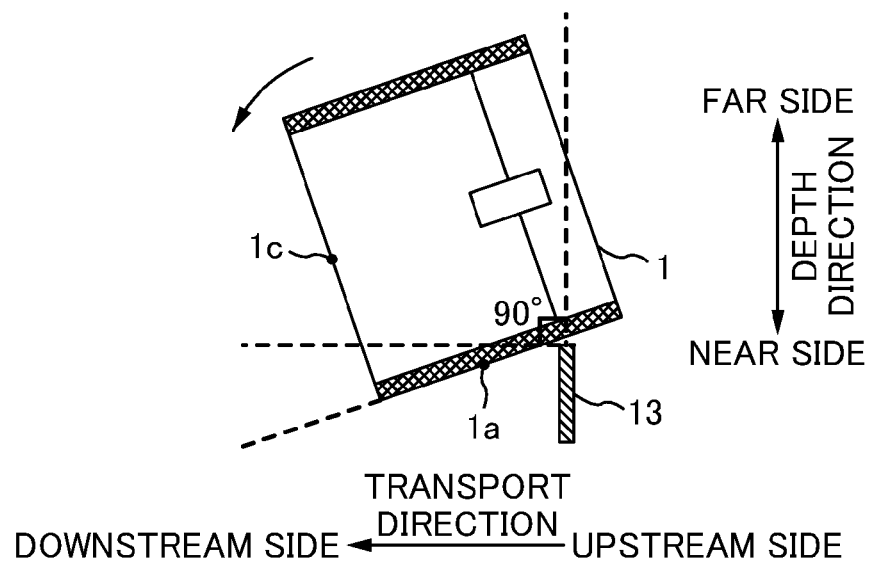
FIG. 5 is an explanatory diagram of a napkin rotating apparatus that does not have a rotation restricting wall.

FIG. 5 is an explanatory diagram of a napkin (napkin 1) rotating apparatus that does not have a rotation restricting wall 14. Here, it is assumed that the napkin 1 is to be rotated through 90 degrees in the counterclockwise direction. Therefore, concerning the napkin 1 after the rotation, as shown in part (A) of FIG. 3, it is preferable that the first edge 1a lies along the transport direction and the third edge 1c lies along the depth direction. However, in the case of a rotation apparatus that does not have the rotation restricting wall 14 as shown in FIG. 5, if the rotational force exerted on the napkin 1 is strong, the napkin 1 will rotate through more than 90 degrees in the counterclockwise direction. As a result, the first edge 1a will not lie along the transport direction and inclines to the near side in the depth direction from the upstream side to the downstream side in the transport direction, and the third edge 1c will not lie along the depth direction and inclines to the upstream side in the transport direction from the far side to the near side in the depth direction.

Accordingly, with the rotating apparatus 10 of the present embodiment, as shown in FIG. 2, the rotation restricting wall 14 that restricts the rotation of the napkin 1 is provided at a position where the rotation restricting wall 14 can come into contact with the first edge 1a of the napkin 1 rotated by the fixed wall 13. Accordingly, even if the rotational force exerted on the napkin 1 is strong and the napkin 1 tends to rotate through an angle of more than 90 degrees in the counterclockwise direction, the first edge 1a of the napkin 1 will come into contact with the rotation restricting wall 14 and the rotation of the napkin 1 is restricted. As a result, an excessive rotation (here, a rotation greater than 90 degrees) of the napkin 1 can be suppressed.

In the rotating apparatus 10 of the present embodiment, the fixed wall 13 has a wall surface lying along the depth direction, and the rotation restricting wall 14 is a wall surface that forms an angle with the wall surface of the fixed wall 13, which angle being based on a desired amount of rotation of the napkin 1. In other words, an angle θ between the wall surface of the fixed wall 13 lying along the depth direction and on the downstream side in the transport direction and the wall surface of the rotation restricting wall 14 lying along the transport direction and on the near side in the depth direction is defined as an angle based on the desired amount of rotation of the napkin 1. Here, since the napkin 1 is to be rotated through 90 degrees in the counterclockwise direction, the angle θ is 90 degrees.

Accordingly, even if the napkin 1 tends to rotate through an angle of more than angle θ (90 degrees), since the first edge 1a of the napkin 1 comes into contact with the rotation restricting wall 14, the napkin 1 can be prevented from being rotated through an angle of more than the desired amount of rotation. In other words, with the rotation restricting wall 14, the napkin 1 can be rotated through the desired amount of rotation.

Figure 6:
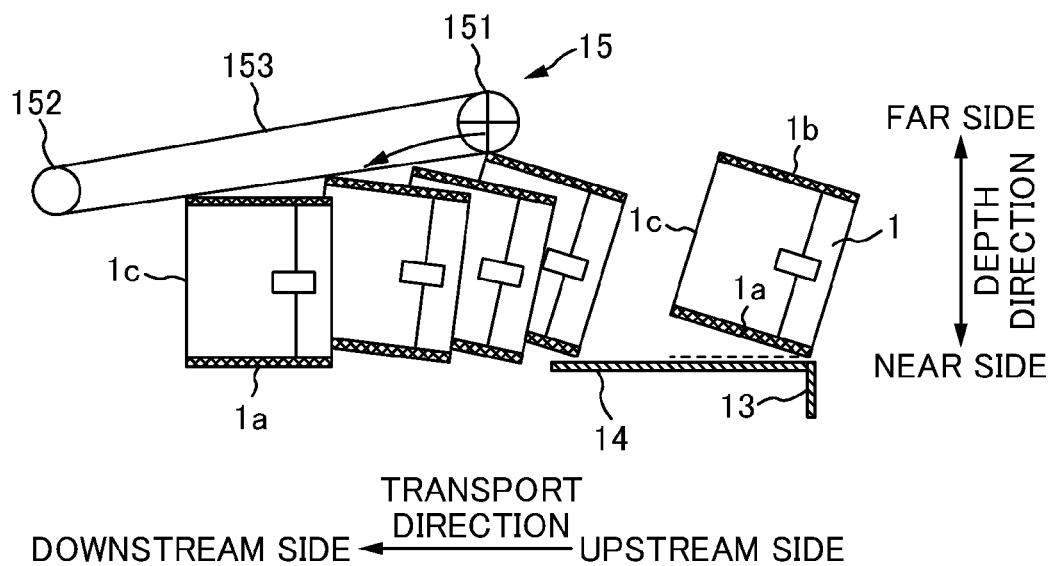
FIG. 6 is an explanatory diagram illustrating a case where an amount of rotation of the napkin rotated by the fixed wall is small.

FIG. 6 is an explanatory diagram illustrating a case where an amount of rotation of the napkin 1 rotated by the fixed wall 13 is small. When the rotational force exerted on the napkin 1 is weak, there may be a case where the napkin 1 only rotates through an angle smaller than 90 degrees in the counterclockwise direction. However, the rotating apparatus 10 of the present embodiment includes the inclined conveyor 15 and the far side inclined wall 16 (corresponds to the first wall section) that are provided at positions on the downstream side in the transport direction with respect to the fixed wall 13 and the rotation restricting wall 14 and on the farther side in the depth direction with respect to the transport belts 11 (i.e., the opposite side to the side where the first edge 1a of the napkin 1 comes into contact with the fixed wall 13). The inclined conveyor 15 and the far side inclined wall 16 are inclined to the near side in the depth direction from the upstream side to the downstream side in the transport direction.

Accordingly, as shown in FIG. 6, even if the napkin 1 rotates through only an angle smaller than the desired amount of rotation, the end section of the napkin 1 on the far side in the depth direction (an intersecting portion between the second edge 1b and the third edge 1c) comes into contact with a surface on the near side in the depth direction of the inclined conveyor 15 (belt 153) and the napkin 1 can be rotated in the counterclockwise direction. As a result, the napkin 1 can be rotated, from a state before coming into contact with the fixed wall 13, through 90 degrees in the counterclockwise direction. In other words, with the inclined conveyor 15 and the far side inclined wall 16, the lack of rotation of the napkin 1 by the fixed wall 13 can be compensated.

As shown in part (A) of FIG. 3, the napkin 1 before coming into contact with the fixed wall 13 is provided in such a manner that the central section C(n) of the napkin 1 in the depth direction and the central section C(b) of the transport belts 11 in the depth direction are at substantially the same position (here, the central section C(n) of the napkin 1 is slightly offset to the near side in the depth direction from the central section C(b) of the transport belts 11). However, the central section C(n) in the depth direction of the napkin 1 after rotation is greatly offset to the far side in the depth direction with respect to the central section C(b) in the depth direction of the transport belts 11. In other words, the napkin 1 that has been rotated by coming into contact with the fixed wall 13 will be located on the far side in the depth direction compared to a state before the rotation. Accordingly, if the central section C(n) of the napkin 1 and the central section C(b) of the transport belts 11 are greatly offset, the napkin 1 cannot be transported in a stable manner.

It is to be noted that the rotating apparatus 10 of the present embodiment has the inclined conveyor 15 and the far side inclined wall 16 inclined to the near side (the transport belts 11 side) in the depth direction from the upstream side to the downstream side in the transport direction. Therefore, as shown in FIG. 3, since the edge (second edge 1b) of the napkin 1 on the far side in the depth direction after the rotation comes into contact with surfaces on the near side in the depth direction of the inclined conveyor 15 (belt 153) and the far side inclined wall 16, the napkin 1 is transported while being offset to the near side in the depth direction (the transport belts 11 side). As a result, the offset between the central section C(n) of the napkin 1 after rotation and the central section C(b) of the transport belts gradually reduces and it is possible to proceed to subsequent processes with the napkin 1 being securely sandwiched between the transport belts 11. In other words, a relative position between the napkin 1 and the transport belt 11 that have been offset by the rotation of the napkin 1 can be returned by the inclined conveyor 15 and the far side inclined wall 16.

Since the napkin 1 rotated by the fixed wall 13 is offset to the far side in the depth direction with respect to the transport belts 11, the wall located on the far side in the depth direction, among the opposing walls that oppose across the transport belts 11, is more likely to come into contact with the napkin 1 than the wall located on the near side. Accordingly, as in the rotating apparatus 10 of the present embodiment, it is preferable that a part of the wall located on the far side in the depth direction with respect to the transport belts 11 is a belt conveyor such as the inclined conveyor 15. Thus, the napkin 1 will not get blocked on the transport path and the napkin 1 can be transported smoothly. Cost can be reduced compared to a case where the wall located on the nearer side in the depth direction respect to the transport belts 11 is also provided as a belt conveyor.

In the rotating apparatus 10, the napkin 1 finally passes between the far side final adjustment wall 17 and the near side final adjustment wall 19. As will be described in detail below, a distance between the far side final adjustment wall 17 and the near side final adjustment wall 19 in the depth direction (D7 in FIG. 2) is smaller than a distance in the depth direction (distance D1 in the width direction in FIG. 1B) of the napkin 1 after rotation (D7<D1). Therefore, a gap will not be produced when the napkin 1 passes between the far side final adjustment wall 17 and the near side final adjustment wall 19, and the central section C(n) of the napkin 1 will pass a central section C(w) in the depth direction between the far side final adjustment wall 17 and the near side final adjustment wall 19.

Therefore, as shown in FIG. 2, it is preferable to determine a relative position between the far side and near side final adjustment walls 17, 19 and the transport belts 11 such that the central section C(b) of the transport belts 11 in the depth direction is located at the central section C(w) in the depth direction between the far side final adjustment wall 17 and the near side final adjustment wall 19. In this manner, as shown in FIG. 3, at part (A), finally, the central section C(n) of the napkin 1 and the central section C(b) of the transport belts 11 can be made to coincide as much as possible. As a result, it is possible to proceed to subsequent processes with the napkin 1 being securely sandwiched between the transport belts 11. Specifically, it is preferable if the central section C(b) of the transport belts 11 passes a position offset from the far side final adjustment wall 17 to the near side in the depth direction by a distance D8 (=D7/2) that is half the distance D7 between the far side final adjustment wall 17 and the near side final adjustment wall 19 in the depth direction, or a position C(w) offset from the near side final adjustment wall 19 to the far side in the depth direction by distance D8.

In the rotating apparatus of the present embodiment, the far side final adjustment wall 17 extending along the transport direction is provided at a position downstream of the inclined conveyor 15 and the far side inclined wall 16 in the transport direction. The near side inclined wall 18 and the near side final adjustment wall 19 (correspond to an opposed wall section) oppose a part of the inclined conveyor 15, the far side inclined wall 16 and the far side final adjustment wall 17 in the depth direction, across the transport belts 11. A distance in the depth direction between the inclined conveyor 15 (belt 153) and the far side inclined wall 16, and the near side inclined wall 18 is configured to be narrower at a downstream position than at an upstream position in the transport direction.

Here, from the upstream side to the downstream side in the transport direction, a breadth formed between the inclined conveyor 15 (belt 153) and the far side inclined wall 16, and the near side inclined wall 18 gradually narrows. Specifically, as shown in FIG. 2, a distance D10 at a second position P2 on the downstream side in the transport direction between a surface of the far side inclined wall 16 on the near side in the depth direction and a surface of the near side inclined wall 18 on the far side in the depth direction is narrower than a distance D9 at a first position P1 on the upstream side in the transport direction between a surface of the belt 153 of the inclined conveyor 15 on the near side in the depth direction and a surface of the near side inclined wall 18 on the far side in the depth direction (D10<D9).

Accordingly, while transporting the napkin 1 smoothly without the napkin 1 getting blocked on the transport path, the position of the napkin 1 that has been offset to the far side in the depth direction with respect to the transport belts 11 can be returned to the transport belt 11 side and an angle of the napkin 1 can be adjusted.

During the process of returning the position of the napkin 1, which has been offset to the far side in the depth direction with respect to the transport belts 11, to the transfer belt 11 side, there is a case of rotating through more than 90 degrees in the counterclockwise direction as compared to the napkin 1 before rotation, as shown in FIG. 3, at part (A). In this case, with the opposed walls having a breadth that gradually narrows, i.e., the inclined conveyor 15 and the far side inclined wall 16, and the near side inclined wall 18, the napkin 1 can be smoothly transferred between the opposed walls extending along the transport direction, i.e., the far side final adjustment wall 17 and near side final adjustment wall 19, while adjusting the angle of the napkin 1. As a result, the napkin 1 is finally transported to the packing process (subsequent process) in a state rotated by the fixed wall 13 by the desired amount of rotation from the stage before rotation (in a state of being rotated through 90 degrees in the counterclockwise direction). Therefore, the processing in the packing process is stabilized and productivity can be improved.

In the rotating apparatus 10 of the present embodiment, the distance in the depth direction (D7 shown in FIG. 2) between the far side final adjustment wall 17 and near side final adjustment wall 19 is less than the length (D1 shown in FIG. 1B) of the third edge 1c that is an edge on the downstream side in the transport direction of the napkin 1 after rotation (napkin 1 including both a portion where the napkin main body section 2 exists and a portion where the napkin main body section 2 does not exist), and greater than or equal to a length (maximum width D2 of the napkin main body section 2 shown in FIG. 1B) of the edge on the downstream side in the transport direction of the napkin main body section 2 after rotation (D2≤D7<D1).

Accordingly, with the far side final adjustment wall 17 and near side final adjustment wall 19, in the napkin 1, the portion where the napkin main body section 2 does not exist (i.e., a portion with only the wrapping material 3, here, the adhesive portion 3A, 3B) is compressed, but the napkin main body section 2 is not compressed. Therefore, degrading of the quality of the napkin 1 can be prevented. On the other hand, if it is only the wrapping material 3 that is compressed, there is no influence on the function as the sanitary napkin, and, for example, when a nonwoven fabric or a polyethylene sheet, etc., is used as the wrapping material 3, the wrapping material 3 can be returned even if it has been compressed.

When the distance D7 in the depth direction of the far side final adjustment wall 17 and near side final adjustment wall 19 (hereinafter, two opposed walls) is less than the width D1 of the napkin 1, the portion of only the wrapping material is compressed and the portion of the napkin 1 where the napkin main body section 2 exists can be laid along the two opposed walls 17 and 19. Accordingly, the a fine adjustment of the angle of the napkin 1 can be performed with the two opposed walls 17 and 19, and finally, the napkin 1 can be transported to the wrapping process (subsequent process) in a state where the napkin 1 is rotated by the desired amount of rotation (in a state where it is rotated through 90 degrees in the counterclockwise direction).

In the rotating apparatus 10 of the present embodiment, as shown in FIG. 2, the distance D8 in the depth direction between a surface on the far side in the depth direction of the near side final adjustment wall 19 and the central section C(b) in the depth direction of the transport belts 11 is greater than a distance D11 between the end section on the far side in the depth direction of the fixed wall 13 and the central section C(b) of the transport belts 11 (D8>D11). In other words, the surface on the far side in the depth direction of the near side final adjustment wall 19 is located on the nearer side in the depth direction with respect to the end section in the depth direction of the fixed wall 13.

In other words, the fixed wall 13 is provided at a position which is comparatively close to the transport belts 11. Therefore, even if the position in the depth direction of the napkin 1 becomes slightly offset at the time of coming into contact with the fixed wall 13, the first edge 1a of the napkin 1 can be securely brought into contact with the fixed wall 13 and the napkin 1 can be rotated.

The napkin 1 after rotation will be located at a farther side in the depth direction with respect to the end section on the far side in the depth direction of the fixed wall 13. Accordingly, the central section C(n) in the depth direction of the napkin 1 after rotation will be offset to the farther side in the depth direction with respect to the central section C(b) in the depth direction of the transport belts 11. Therefore, by providing the surface on the far side in the depth direction of the near side final adjustment wall 19 at a position on the nearer side in the depth direction with respect to the end section in the depth direction of the fixed wall 13, the central section C(n) of the napkin 1 after rotation can be brought closer to the central section C(b) of the transport belts 11. As a result, the napkin 1 can be transferred to the subsequent process while being securely sandwiched between the transfer belts 11.

===Variants===

Figure 7A:
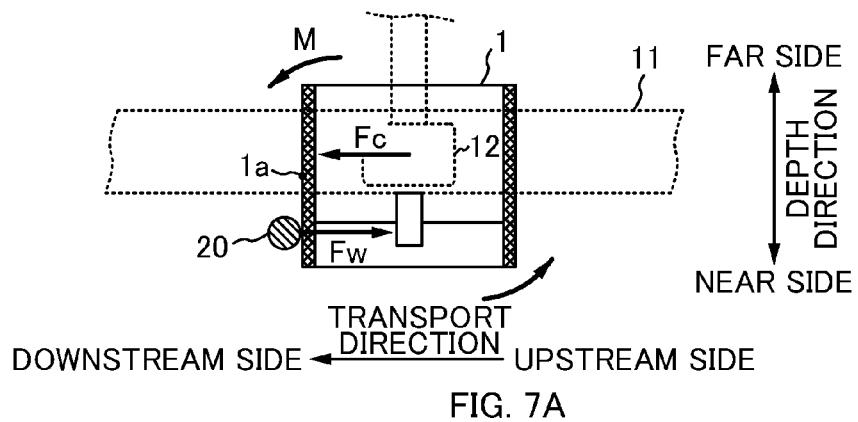
FIGS. 7A to 7C are explanatory diagrams illustrating variants.

FIG. 7A is an explanatory diagram illustrating a variant of a fixed member that rotates the napkin 1. In the embodiment described above, as shown in FIG. 4, the fixed member is exemplified by the fixed wall 13 having the fall surface (contacting surface 13a) extending along the depth direction, but it is not limited thereto. For example, as shown in FIG. 7A, the fixed member 20 may be a rod-like member that extends in the up-down direction (a direction penetrating through the plane of paper of FIG. 7A) of the rotating apparatus. By fixing such rod-like fixed member 20 at a predetermined position in the transport direction, a portion of the edge (first edge 1a) on the downstream side in the transport direction of the napkin 1, which portion being exposed from the transport belts 11, can be brought into contact with the peripheral surface of the fixed member 20 and the napkin 1 can be rotated in the counterclockwise direction.

Figure 7B:
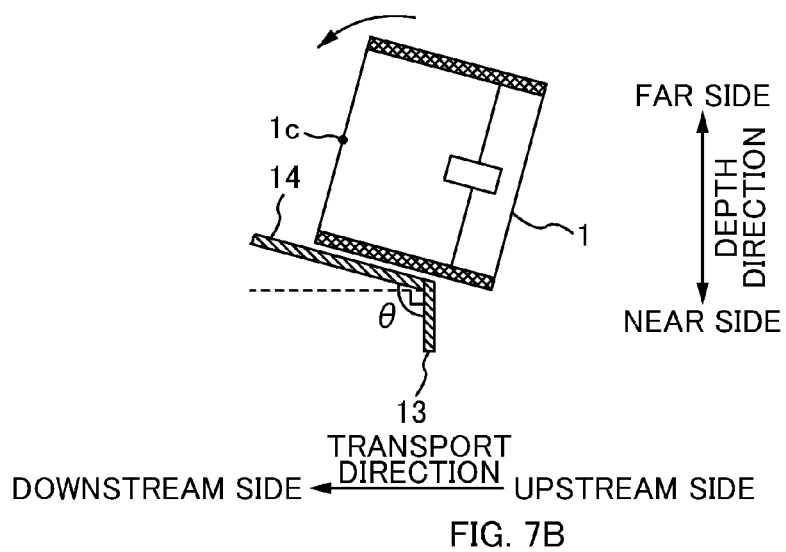

FIG. 7B is an explanatory diagram illustrating a variant of the amount of rotation of the napkin 1. In the embodiment described above, the embodiment in which the napkin 1 is rotated through 90 degrees in the counterclockwise direction is shown by way of example, but it is not limited thereto. For example, as shown in FIG. 7B, the napkin 1 may be rotated through an angle smaller than 90 degrees in the counterclockwise direction. In such a case, as shown in FIG. 7B, it is preferable that the angle θ between the surface of the fixed wall 13 lying along the depth direction and on the downstream side in the transport direction and the surface of the rotation restricting wall 14 lying along the transport direction and on the near side in the depth direction is an angle greater than 90 degrees. Thus, the rotation of the napkin 1 is restricted by the rotation restricting wall 14 before the napkin 1 rotates through 90 degrees in the counterclockwise direction.

Further, when it is desired to rotate the napkin 1 through an angle greater than 90 degrees in the counterclockwise direction (not shown), it is preferable that the angle θ between the fixed wall 13 and the rotation restricting wall 14 is an angle smaller than 90 degrees.

In this manner, it is preferable that the angle θ between the fixed wall 13 and the rotation restricting wall 14 is an angle corresponding to the desired amount of rotation.

In the embodiment described above, the embodiment in which the napkin 1 is rotated in the counterclockwise direction is shown by way of example, but it is not limited thereto. For example, in the rotating apparatus 10 shown in FIG. 2, the napkin 1 can be rotated in the clockwise direction by providing the fixed wall 13 at a position on the farther side in the depth direction with respect to the transport belts 11.

Figure 7C:
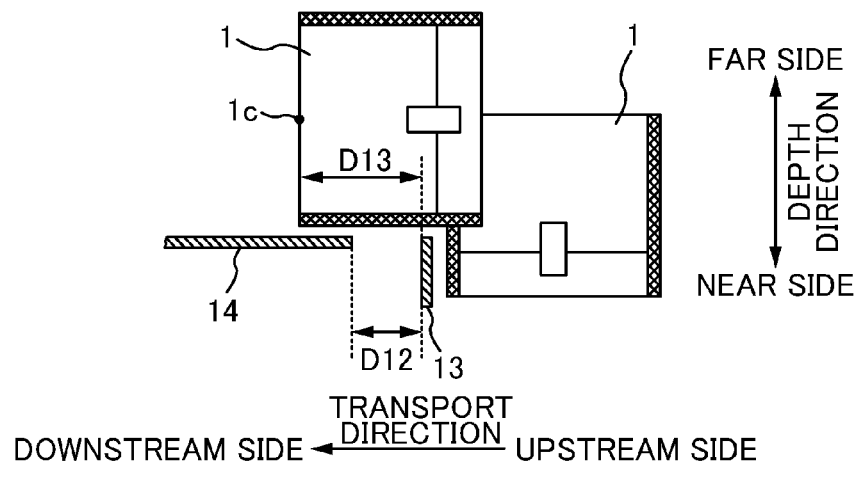

FIG. 7C is an explanatory diagram illustrating a variant of an arrangement of the fixed wall 13 and the rotation restricting wall 14. In the embodiment described above, as shown in FIG. 2, the fixed wall 13 and the rotation restricting wall 14 are arranged continuously in the transport direction, but it is not limited thereto. For example, as shown in FIG. 7C, the fixed wall 13 and the rotation restricting wall 14 may be arranged in a spaced apart manner. In doing so, it is preferable that a distance D12 in the transport direction between the fixed wall 13 and the rotation restricting wall 14 is shorter than a length D13 from the edge (third edge 1c) of the napkin 1 after rotation on the downstream side in the transport direction to the surface of the fixed wall 13 on the downstream side in the transport direction (D12<D13). In this manner, the napkin 1 can be prevented from being caught at the spaced part section of the fixed wall 13 and the rotation restricting wall 14, and the napkin 1 can be smoothly transported.

Figure 8A:
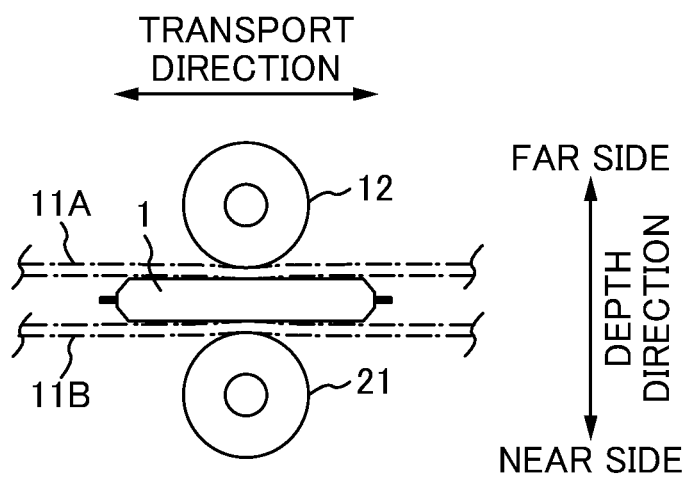
FIGS. 8A and 8B are explanatory diagrams illustrating variants.
Figure 8B:
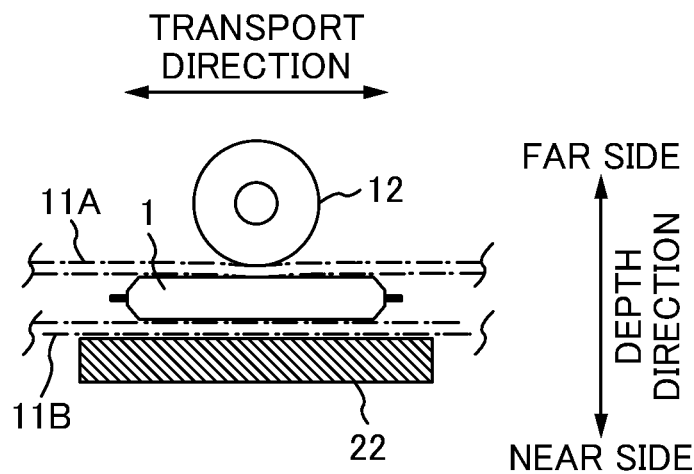

FIGS. 8A and 8B are explanatory diagrams illustrating variants of a pressing member that presses the napkin 1 in the thickness direction when the napkin 1 rotates. In the embodiment described above, the pressing member is exemplified by the pressing roller 12, but it is not limited thereto and other members may be used. In the embodiment described above, as shown in part (C) of FIG. 3, there is a space on a side of the pressing roller 12 opposite to the transport belts 11, but it is not limited thereto. For example, as shown in FIG. 8A, a different pressing roller 21 may be provided at a position opposing the pressing roller 12 across the transfer belts 11A, 11B. As shown in FIG. 8B, a receiving section 22 (e.g., a sheet metal having a surface parallel to the wide surface of the transfer belts 11, etc.,) may be provided at a position opposing the pressing roller 12 across the transfer belts 11A, 11B. In these cases, when the napkin 1 comes into contact with the fixed wall 13, a force exerted by the transport belts 11 to sandwich the napkin 1 can be increased and thus the slippage between the transport belts 11 and the napkin 1 can be prevented. As a result, the force (Fc shown in FIG. 4) that causes the napkin 1 to move to the downstream side in the transport direction can be exerted on the napkin 1 and the napkin 1 can be securely rotated.

Figure 9:
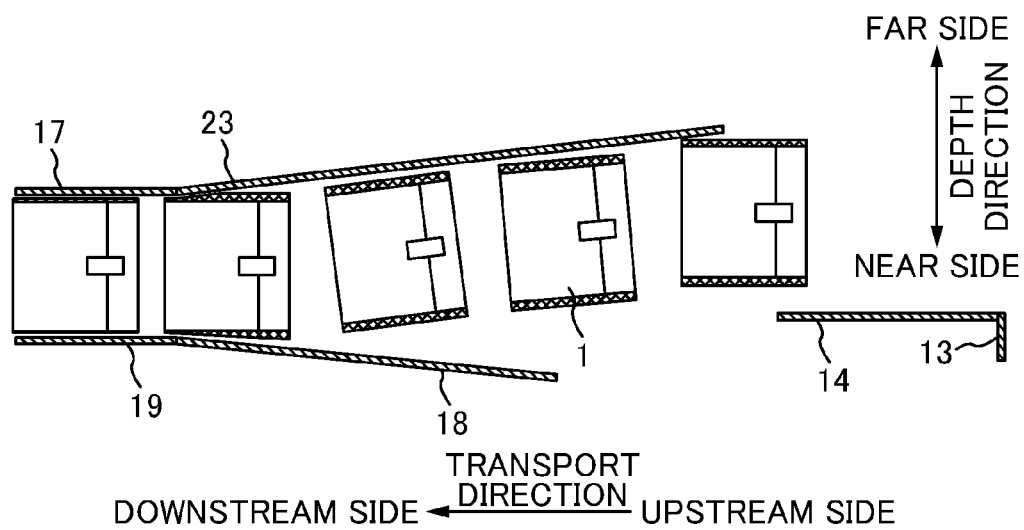
FIG. 9 is an explanatory diagram of a variant.

FIG. 9 is an explanatory diagram of a variant of an inclined wall (first wall section) located on the far side in the depth direction. In the embodiment described above, as shown in FIG. 2, the inclined wall is exemplified by the inclined conveyor 15 and the far side inclined wall 16 (a wall that is inclining to the near side in the depth direction from the upstream side to the downstream side in the transport direction) located on the far side in the depth direction, but it is not limited thereto. As shown in FIG. 9, a part of the inclined wall located on the far side in the depth direction may not be a belt conveyor, but may be a wall 23 formed by a sheet metal member.

Further, the inclined wall on the near side in the transport direction (near side inclined wall 18 shown in FIG. 9) may be a belt conveyor. Since the napkin 1 rotated by the fixed wall 13 will be offset to the far side in the depth direction with respect to the transport belts 11, the wall located on the near side in the depth direction has a less region in contact with the napkin 1, and it is difficult for the napkin 1 to get caught. Therefore, the wall located on the near side in the depth direction may be a wall that extends along the transport direction and not inclined.

In the embodiment described above, the rotation restricting wall 14 that prevents an excessive rotation of the napkin 1 is provided, but it is not limited thereto and the rotating apparatus may be a rotating apparatus that does not have the rotation restricting wall 14 as illustrated in FIG. 5. The rotating apparatus may be a rotating apparatus that does not have walls (the inclined conveyor 15, the far side inclined wall 16, the far side final adjustment wall 17, the near side inclined wall 18 and the near side final adjustment wall 19) opposing in the depth direction across the transport belts 11.

Other Embodiments

In the description above, the absorbent article rotating apparatus and the method of rotating absorbent article of the aspects of the invention have been described based on the above-mentioned embodiments. The embodiments of the present invention are simply for facilitating the understanding of the present invention and are not in any way to be construed as limiting the present invention. The present invention may variously be modified or altered without departing from its spirit and encompass equivalents thereof.

In the above-mentioned embodiments, the embodiment in which the individually wrapped sanitary napkin (FIG. 1B) is rotated as an exemplary absorbent article has been described. However, it is not limited thereto and the absorbent article rotating apparatus and the method of rotating absorbent article of the aspects of the invention may be applied to, for example, diapers, sanitary napkins that are not individually wrapped or sanitary napkins that are not folded.

REFERENCE SIGNS LIST 1 napkin (absorbent article),
2 napkin main body section (main body section),
3 wrapping member, 4 wing section, 5 protection sheet, 6 tape,
3A adhered section, 3B adhered section, 1a first edge, 1b second edge, 1c third edge, 1d forth edge,
10 rotating apparatus, 11 transporting belt (a pair of belts),
11A upper transport belt, 11B lower transport belt,
12 pressing roller (pressing member), 13 fixing wall (fixing member),
14 rotation restricting wall (rotation restricting section),
15 inclined conveyor (first wall section),
151 driving roller, 152 driven roller, 153 belt,
16 far side inclined wall (first wall section),
17 far side final adjustment wall (second wall section),
18 near side inclined wall (opposed wall section),
19 near side final adjustment wall (opposed wall section),
20 fixing member, 21 pressing roller,
22 receiving section, 23 wall

The invention claimed is:

1. An absorbent article rotating apparatus, comprising:
a transporting section including a pair of belts and configured to transport an absorbent article along a transport direction with the absorbent article being sandwiched between the pair of belts;
a fixed member configured to rotate the absorbent article by coming into contact with a portion of an edge of the absorbent article, the portion being exposed from the belts, the edge being at a downstream side in the transport direction, the fixed member being fixed at a predetermined position in the transport direction; and
a pressing member,
wherein
the pair of belts is configured to sandwich the absorbent article in a thickness direction of the absorbent article, and
the pressing member is configured to press the absorbent article in the thickness direction via the belts when the edge of the absorbent article and the fixed member come into contact with each other.

2. An absorbent article rotating apparatus according to claim 1, further comprising:
a rotation restricting section configured to restrict rotation of the absorbent article, the rotation restricting section being provided at a position where the rotation restricting section is contactable with the edge of the absorbent article rotated by the fixed member.

3. An absorbent article rotating apparatus according to claim 2, wherein the fixed member has a wall surface lying along an intersecting direction that intersects with the transport direction, the rotation restricting section being a wall surface that forms an angle with the wall surface of the fixed member, the angle being based on a predetermined amount of rotation of the absorbent article.

4. An absorbent article rotating apparatus according to claim 1, further comprising a first wall section,
wherein
the fixed member is configured to come into contact with the edge of the absorbent article at the portion of the edge exposed from the belts at a first side in an intersecting direction that intersects with the transport direction,
the first wall section is positioned downstream of the fixed member in the transport direction and positioned more towards a second side in the intersecting direction than the belts, and
the first wall section is inclined to the first side in the intersecting direction from an upstream side in the transport direction to the downstream side.

5. An absorbent article rotating apparatus according to claim 4, further comprising:
a second wall section provided at a position downstream of the first wall section in the transport direction; and
an opposed wall section that opposes at least a part of the first wall section as well as the second wall section across the belts in the intersecting direction,
a gap between the first wall section and the opposed wall section in the intersecting direction being narrower at a position on the downstream side in the transport direction than at a position on the upstream side.

6. An absorbent article rotating apparatus according to claim 5, wherein
a gap in the intersecting direction between the opposed wall section opposing the second wall section and a central section of the belts in the intersecting direction is greater than a gap in the intersecting direction between an end section of the fixed member on the second side in the intersecting direction and the central section of the belts.

7. A method of rotating an absorbent article, the method comprising:
transporting an absorbent article along a transport direction with the absorbent article being sandwiched between a pair of belts, the pair of belts sandwiching the absorbent article in a thickness direction of the absorbent article; and
rotating the absorbent article by causing a portion of an edge of the absorbent article to come into contact with a fixed member, the portion being exposed from the belts, the edge being at a downstream side in the transport direction, the fixed member being fixed at a predetermined position in the transport direction,
wherein
the absorbent article is pressed by a pressing member in the thickness direction via the belts when the edge of the absorbent article and the fixed member come into contact with each other.

* * * * *